(12) United States Patent
Tobler et al.

(10) Patent No.: US 6,285,896 B1
(45) Date of Patent: Sep. 4, 2001

(54) FETAL PULSE OXIMETRY SENSOR

(75) Inventors: David R. Tobler; Mohamed K. Diab, both of Mission Viejo; Robert J. Kopotic, Jamul, all of CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/348,767

(22) Filed: Jul. 7, 1999

Related U.S. Application Data

(60) Provisional application No. 60/092,644, filed on Jul. 13, 1998.

(51) Int. Cl.$^7$ ............................................. A61B 5/00
(52) U.S. Cl. ........................... 600/338; 600/310; 600/323
(58) Field of Search ................................. 600/310, 313, 600/322, 323, 338, 339, 340, 341, 342, 334

(56) References Cited

U.S. PATENT DOCUMENTS

| | | |
|---|---|---|
| 4,537,197 | 8/1985 | Hulka . |
| 4,658,825 | 4/1987 | Hochberg et al. . |
| 4,938,218 | 7/1990 | Goodman et al. . |
| 5,099,842 | 3/1992 | Mannheimer et al. . |
| 5,109,849 | 5/1992 | Goodman et al. . |
| 5,131,391 * | 7/1992 | Sakai et al. ........................... 600/334 |
| 5,154,175 | 10/1992 | Gunther . |
| 5,193,542 | 3/1993 | Missanelli et al. . |
| 5,228,440 | 7/1993 | Chung et al. . |
| 5,247,932 | 9/1993 | Chung et al. . |
| 5,267,563 * | 12/1993 | Swedlow et al. ........................... 600/334 |
| 5,361,757 | 11/1994 | Smith et al. . |
| 5,377,673 | 1/1995 | Van Dell et al. . |
| 5,377,675 | 1/1995 | Ruskewicz et al. . |
| 5,411,024 | 5/1995 | Thomas et al. . |
| 5,419,322 | 5/1995 | Joseph et al. . |
| 5,421,329 * | 6/1995 | Casciani et al. ........................... 600/338 |
| 5,425,362 | 6/1995 | Siker . |

(List continued on next page.)

FOREIGN PATENT DOCUMENTS

| | | |
|---|---|---|
| 91/18549 | 12/1991 | (WO) . |
| 94/18884 | 9/1994 | (WO) . |
| WO 96/41566 | 12/1996 | (WO) . |

OTHER PUBLICATIONS

Dassel, et al., "Reflectance Pulse Oximetry in Fetal Lambs", *Pediatric Research*, vol. 31, No. 3, 1992 pp. 266–269.

Gardosi, J. et al., "Adaptation of PPulse Oximetry for Fetal Monitoring During Labour", *The Lancet*, vol. 337, May 25, 1991, pp. 1265–1267.

Johnson, N. et al., "Monitoring the Fetus with a Pulse Oximeter During a Caesarean Section", *British Journal of Obsterics and Gynaecology*, vol. 97, Jul. 1990, pp. 653–658.

(List continued on next page.)

*Primary Examiner*—Eric F. Winakur
(74) *Attorney, Agent, or Firm*—Knobbe, Martens, Olson & Bear, LLP

(57) ABSTRACT

A sensor provides pulse oximetry measurements from the presenting portion of a fetus. In particular, a spiral probe is designed to attach the sensor to the fetal scalp. In one sensor configuration, a light emitting region of the probe embedded in the scalp in conjunction with a light detector located at the scalp surface measures absorption from a larger volume of the scalp tissue than conventional fetal sensors. In another sensor configuration, light emitting and light collecting regions of the probe embedded in the scalp are angled with respect to the scalp surface to measure absorption from a larger volume and deeper layers of the scalp tissue than conventional fetal sensors. These sensors increase the likelihood of measuring blood volume changes occurring in larger arterioles versus smaller arterioles or capillaries, yielding a representative measurement of central arterial oxygen saturation. These sensors also reduce the calibration errors caused by a low blood fraction. Localized arteriolar flow is stimulated with heat or vasodilating substances to reduce the effects of localized oxygen consumption and to increase blood fraction. A three-wavelength sensor is utilized to detect a low blood fraction condition.

23 Claims, 14 Drawing Sheets

U.S. PATENT DOCUMENTS

| | | |
|---|---|---|
| 5,474,065 | 12/1995 | Meathrel et al. . |
| 5,494,032 | 2/1996 | Robinson et al. . |
| 5,497,771 | 3/1996 | Rosenheimer . |
| 5,529,064 | 6/1996 | Rall et al. . |
| 5,551,424 | 9/1996 | Morrison et al. . |
| 5,634,459 | 6/1997 | Gardosi . |
| 5,662,103 | 9/1997 | Smith et al. . |
| 5,687,719 | 11/1997 | Sato et al. . |
| 5,727,547 | 3/1998 | Levinson et al. . |
| 5,743,260 | 4/1998 | Chung et al. . |
| 5,776,058 | 7/1998 | Levinson et al. . |
| 5,813,980 | 9/1998 | Levinson et al. . |
| 5,823,952 | 10/1998 | Levinson et al. . |
| 5,833,622 | 11/1998 | Meathrel et al. . |
| 5,839,439 | 11/1998 | Nierlich et al. . |
| 5,851,179 | 12/1998 | Ritson et al. . |

OTHER PUBLICATIONS

Johnson, N. et al., "The Accuracy of Fetal Pulse Oximetry in the Second State of Labour", *J. Perinat. Med.*, vol. 19, 1991, pp. 297–303.

Johnson, N. et al., "Fetal Monitoring with Pulse Oximetry", *British Journal of Obstetrics and Gynaecology*, Jan. 1991, vol. 98, pp. 36–41.

Lurie, Samuel et al., "Fetal Oximetry Monitoring: A New Wonder or Another Mirage?", *Obstetrical and Gynecological Survey*, vol. 51, No. 6, 1996.

Richardson, Bryan et al., "Fetal Oxygen Saturation and Fractional Extraction at Birth and the Relationship to Measures of Acidosis", *Am. J. Obstet. Gynecol.*, vol. 178, No. 3, Mar. 1998.

Nellcor product brochure, "Introduction to Fetal Oxygen Saturation Monitoring".

* cited by examiner

US 6,285,896 B1

FETAL PULSE OXIMETRY SENSOR

PRIORITY CLAIM

This application claims the benefit of U.S. Provisional Application No. 60/092,644, filed Jul. 13, 1998.

BACKGROUND OF THE INVENTION

Physicians have long relied on intrapartum fetal surveillance for an early warning of complications arising during labor. The ultimate goal of fetal monitoring is to prevent damage to the most vital and sensitive organs, such as the brain and the heart, by detecting a decreased oxygen supply to these organs before the onset of cell damage. Some causes of fetal hypoxia are umbilical cord compression, placental insufficiency or hypertonia of the uterus. Early examples of fetal monitoring are intermittent auscultation of fetal heartbeat, electronic monitoring of fetal ECG and heart rate, and scalp blood pH. These techniques are based on the assumption that fetal hypoxia, leads to fetal acidemia and also to specific pathologic fetal ECG and heart rate patterns. These indirect techniques, however, are unsatisfactory because it is only after hypoxia has occurred for some time that it is reflected in adverse changes in the heart rate or blood pH.

More recently, fetal assessment has evolved to the direct measurement of fetal oxygen status using pulse oximetry. Pulse oximetry instrumentation, which provides a real-time measurement of arterial oxygen saturation, has become the standard of care for patient vital sign monitoring during anesthesia and in neonatal and adult critical care. A pulse oximetry system consists of a sensor attached to a patient, a monitor, and a cable connecting the sensor and monitor. The sensor typically has red and infrared light emitting diodes that illuminate a tissue site and a photodiode detector that measures the intensity of that light after absorption by the pulsatile vascular bed at the tissue site. From these measurements, the oxygen saturation of arterial blood can be calculated.

SUMMARY OF THE INVENTION

Pulse oximetry as applied to fetal intrapartum monitoring must overcome several significant and interrelated obstacles not faced by pulse oximetry as applied to adults, children, infants and neonates. These obstacles include attaching the sensor to a readily accessible tissue site, obtaining a representative measurement of central arterial oxygen saturation at that site, and calibrating the sensor. Pulse oximetry sensors are conventionally attached, for example, to an adult finger or a neonate foot using a self-adhesive mechanism that wraps around the tissue site. Sensor attachment to a fetus in this manner is impractical if not impossible. The uterine environment is fluid filled and the skin of the fetus is coated with vernix, an oily substance. Further, the presenting portion of the fetus is typically the crown of the head, which yields only the fetal scalp as a readily accessible tissue site. A number of mechanisms have been developed to overcome these impediments to attachment of a pulse oximetry sensor to the fetus. These include suction cups, clamps and vacuum devices for scalp attachment. There are also devices that slide beyond the fetus presenting portion, wedging between the uterine wall and the fetus.

FIG. 1 illustrates a scalp attachment mechanism used in conjunction with a fetal ECG sensor but also applicable to fetal pulse oximetry. The sensor assembly 100 consists of a fetal sensor 110, a drive tube 120, a guide tube 130, and interconnecting conductors 140. The fetal sensor 110 has a spiral probe 112 attached to a sensor base 114. The probe 112 is utilized to attach the sensor 110 to the fetal scalp and also functions as an ECG electrode. The sensor base 114 is removably connected to the drive tube 120 by a fin 116 that fits within slots 122 of the drive tube 120. The sensor 110 and connected drive tube 120 are movably contained within the guide tube 130. The interconnecting wires 140 are attached at one end to the sensor base 114, and one of the conductors 140 is electrically connected to the probe 112. The other end of the conductors 140 are threaded through the inside of the drive tube 120 and the guide tube 130, extending from the end of the drive tube 120 opposite the sensor 110.

When using the sensor assembly 100 to attach the sensor 110 to a fetus, a physician first inserts the guide tube 130 into the mother's birth canal toward the cervix until the guide tube forward end 132 makes contact with the fetal head. Holding the forward end 132 stationary, the physician then inserts the drive tube 120 and attached sensor 110 into the guide tube 130, pushing the rear end of the drive tube 120 forward until the spiral probe 112 makes contact with the fetal scalp. The physician then rotates the drive tube 120 causing the spiral probe 112 to embed into the fetal epidermis. Thereafter, the physician removes the guide tube 130 and drive tube 120 from the mother, sliding these tubes off the conductors 140, leaving the sensor attached to the fetus with the wires 140 extending from the mother. The conductors 140 are then attached to a heart rate monitor.

Mere attachment of a pulse oximetry sensor to the fetal scalp, however, does not insure that the sensor can measure a representative value of central arterial oxygen saturation from that site. There are many potential tissue sites for scalp attachment of a fetal sensor, but conventional fetal sensors are prone to inconsistent, site-dependent saturation readings. Further, conventional fetal sensors are prone to measurements of oxygen saturation that are dependent on localized oxygen consumption and, therefore, may not be representative of central arterial oxygen supply. These problems are the result of the nonuniform vascularization of the scalp, as explained with respect to FIG. 2A, below. Further, based upon the various presentations of the fetal head, uterine, cervical and vaginal pressures to the head may be unequally applied, resulting in portions of the scalp having compromised perfusion.

FIG. 2A depicts the large arteries of the scalp, which are located in the deeper tissue layers. Unlike an adult fingertip or a neonatal foot, the fetal scalp does not provide a specific tissue site with a readily located large artery from which to take pulse oximetry measurements. As shown in FIG. 2A, the scalp contains a web of large arteries separated by significant areas perfused only by branching small arteries, arterioles and capillaries. Because arterial vascularization of the scalp is not uniform, different scalp sites yield measurements taken from various sized arteries and under conditions of differing blood volumes with respect to tissue volume (blood fraction). This, in turn, affects the measured saturation, as described below with respect to FIG. 2B.

FIG. 2B is adapted from *Microvascular and Tissue Oxygen Distribution,* M. Intaglietta, P. Johnson, and R. Winslow, Cardiovascular Research, Elsevier Science 1996, which depicts the distribution of oxygen in the arterioles starting from the larger A1 vessels to the smallest A4 precapillary vessels and capillaries. FIG. 2B is composed of interconnected graphs 210, 260. The graph 210 has an x-axis 212 that corresponds to $pO_2$ and a y-axis 214 that corresponds blood vessel type. The graph 260 has an x-axis 262 that also corresponds to $pO_2$ and is aligned with the x-axis 212 of graph 210. The y-axis 264 of graph 260 corresponds to oxygen saturation. The length of the bars 218 of graph 210 indicate the $pO_2$ of the blood according to vessel size. The oxygen dissociation curve 268 in the graph 260 illustrates the oxygen binding characteristics of blood hemoglobin.

FIG. 2B shows that the oxygen saturation of blood in the microcirculation is dependent on vessel size, indicating the role of the various vessels with respect to tissue oxygenation. In particular, blood flowing through the smaller arterioles and capillaries has been partially desaturated by vessel and localized tissue oxygen consumption. Whereas larger arterioles contain more highly saturated blood reflective of the central oxygen supply. FIGS. 2A and 2B demonstrate that a fetal pulse oximetry sensor that measures a relatively small tissue volume or only superficial tissue layers containing capillaries is less likely to obtain a representative oxygen saturation measurement and more likely to suffer site dependent variations. Further, such a sensor may measure a tissue site with a low blood fraction that renders the pulse oximeter calibration curve invalid.

To compute peripheral arterial oxygen saturation, denoted $Sp_aO_2$, pulse oximetry relies on the differential light absorption of oxygenated hemoglobin, $HbO_2$, and deoxygenated hemoglobin, Hb, to compute their respective concentrations in the arterial blood. This differential absorption is measured at the red and infrared wavelengths of the sensor. In addition, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might further comprise skin, muscle, bone, venous blood, fat, pigment, etc., each of which also absorbs light. It is assumed that the background absorption due to these surrounding tissues is invariant and can be ignored. Accordingly, blood oxygen saturation measurements are based upon a ratio of the time-varying or AC portion of the detected red and infrared signals with respect to the time-invariant or DC portion. This AC/DC ratio normalizes the signals and accounts for variations in light path lengths through the measured tissue. Further, a ratio of the normalized absorption at the red wavelength over the normalized absorption at the infrared wavelength is computed:

$$R=(Red_{AC}/Red_{DC})/(IR_{AC}/IR_{DC}) \qquad (1)$$

where $Red_{AC}$ and $IR_{AC}$ are the root-mean-square (RMS) of the corresponding time-varying signals. This "red-over-infrared, ratio-of-ratios" cancels the pulsatile signal. The desired $Sp_aO_2$ measurement is then computed from this ratio.

Conventionally, the relationship between the quantity measured by pulse oximeters, R, and the desired oxygen saturation measurement, $Sp_aO_2$, is determined by statistical regression of experimental measurements obtained from human volunteers using calibrated measurements of oxygen saturation. In a pulse oximeter device, this empirical relationship can be stored as a "calibration curve" in a read-only memory (ROM) look-up table so that $Sp_aO_2$ can be directly derived from R. This calibration curve is qualitatively justified by the Beer-Lambert's law of absorption, outlined below, which can yield an approximation to the calibration curve. However, the assumptions underlying Beer-Lambert's law may be invalid for conventional fetal pulse oximetry sensors under certain conditions.

According to the Beer-Lambert law of absorption, the intensity of light transmitted through an absorbing medium is given by:

$$I=I_0 \exp(-\Sigma_{i=1}^{N} \epsilon_{i,\lambda} c_i x_i) \qquad (2)$$

where $I_0$ is the intensity of the incident light, $\epsilon_{i,\lambda}$ is the absorption coefficient of the $i^{th}$ constituent at a particular wavelength $\lambda$, $c_i$ is the concentration coefficient of the $i^{th}$ constituent and $x_i$ is the optical path length of the $i^{th}$ constituent. As stated above, assuming the absorption contribution by all constituents but the arterial blood is constant, taking the natural logarithm of both sides of equation (2) and removing time invariant terms yields:

$$\ln(I)=-[\epsilon_{HbO2,\lambda}C_{HbO2}+\epsilon_{Hb,\lambda}C_{hb}]x(t) \qquad (3)$$

Measurements taken at both red and infrared wavelengths yield:

$$RD(t)=-[\epsilon_{HbO2,RD}C_{HbO2}+\epsilon_{Hb,RD}C_{hb}]x_{RD}(t) \qquad (4)$$

$$IR(t)=-[\epsilon_{HbO2,IR}C_{HbO2}+\epsilon_{Hb,IR}C_{hb}]x_{IR}(t) \qquad (5)$$

Taking the ratio $R=RD(t)/IR(t)$ and assuming $x_{RD}(t) \approx x_{IR}(t)$ yields:

$$R=[\epsilon_{HbO2,RD}C_{HbO2}+\epsilon_{Hb,RD}C_{Hb}]/[\epsilon_{HbO2,IR}C_{HbO2}+\epsilon_{HB,IR}C_{Hb}] \qquad (6)$$

The relationship between arterial oxygen saturation and hemoglobin concentration can be expressed as:

$$Sp_aO_2=C_{HbO2}/(C_{Hb}+C_{HbO2}) \qquad (7)$$

Assuming that:

$$C_{HbO2}+C_{Hb}=1 \qquad (8)$$

then equation (7) can be solved in terms of R:

$$Sp_aO_2=[R\epsilon_{Hb,IR}-\epsilon_{Hb,RD}]/[(\epsilon_{HbO2,RD}-\epsilon_{Hb,RD})+R(\epsilon_{Hb,IR}-\epsilon_{HbO2,IR})] \qquad (9)$$

Thus, Beer-Lambert's law indicates that there is a fixed relationship between oxygen saturation and the measured value R. It is this relationship that is expressed as the calibration curve stored in the pulse oximeter, as described above.

Beer-Lambert's law is based on an absorption model and does not account for tissue scattering. Blood significantly absorbs the red and infrared wavelengths of interest. Thus, when there is a sufficient blood fraction, the volume of blood as compared with the volume of other tissues, the average photon path length is relatively short, and scattering only has a second-order effect on the intensity of the detected signal. When the blood fraction is small, however, scattering effects cannot be ignored. Using a photon-diffusion model, the relationship between R and SpaO2 can be expressed as:

$$Sp_aO_2=[R\epsilon_{Hb,IR}-K\epsilon_{Hb,RD}]/[K(\epsilon_{HbO2,RD}-\epsilon_{Hb,RD})+R(\epsilon_{Hb,IR}-\epsilon_{HbO2,IR})] \qquad (10)$$

where $K=K(\Sigma_{IR}, \Sigma_R, \alpha_{IR}, \alpha_R, d)$
adapted from *Simple Photon Diffusion Analysis of the Effects of Multiple Scattering on Pulse Oximetry*, Joseph M. Schmitt, IEEE Transactions on Biomedical Engineering, December 1991. Equations (9) and (10) differ by the term K appearing in the numerator and denominator of equation (10). K is a function of tissue thickness, d, and the optical properties of the tissue medium, including the wavelength-dependent scattering coefficients, $\Sigma$, and attenuation coefficients, $\alpha$, of the tissue. The photon diffusion model accounts for the distances traversed by source photons before they are captured by the detector, as determined by both absorption and scattering mechanisms in the tissue. By contrast, in the Beer-Lambert model, the optical path length at the red and infrared wavelengths is assumed to be a constant independent of the tissue optical properties. The photon-diffusion model predicts a blood-fraction dependent calibration curve.

FIG. 2C illustrates a graph 280, also adapted from the Schmitt reference cited above, which shows the effect of a change in blood fraction on the pulse oximeter calibration curve. The graph 280 has an x-axis 282 corresponding to oxygen saturation and a y-axis 284 corresponding to the measured ratio, R. A first curve 292 represents the calibration curve for a low blood volume (1%) and a second curve 294 represents the calibration curve for a high blood volume (5%). A fetal sensor that measures a small tissue volume or only the surface tissue layers could be measuring a relatively low blood fraction or a relatively large blood fraction depending on sensor placement. FIG. 2C illustrates that such a sensor may provide measurements that do not correspond to the calibration curve of the connected pulse oximeter. Correspondingly, such a sensor configuration would obtain saturation readings offset from the actual saturation. Further, these saturations could be time varying, as tourniquet-like pressures on the head during labor alter the flow of blood to the tissue site.

FIGS. 3, 4A and 4B illustrate several fetal pulse oximetry sensor configurations that are inherently susceptible to the problems described above. These sensors can be classified as either reflectance mode or transmission mode sensors. Reflectance mode sensors have the emitters and detector placed next to each other on the tissue site. Transmission mode sensors have the emitters and detector on opposite sides of a tissue site. Both reflectance and transmission mode sensors transmit light into a pulsatile vascular bed, where it is absorbed, reflected, and scattered by tissue and blood. With reflectance mode sensors, only that fraction of emitted light that is reflected back to the detector is relevant. With transmission mode sensors, that fraction of emitted light that is not absorbed or scattered away from the detector is relevant.

FIG. 3 depicts the configuration of a reflectance mode pulse oximetry sensor attached to a fetal scalp 10. Emitters 360 and a detector 370 are co-located against the scalp surface 12. Light transmitted from the emitters 360 follows the paths 380 in reaching the detector 370. As a result of dependence on scattering, the volume of measured fetal tissue is relatively small and limited to the surface layers of the scalp. Further, reflectance mode sensors have several drawbacks. A gap between sensor and skin may result in interference from ambient light. In the birth canal, however, there is an absence of ambient light interference. Nevertheless, a portion of light from the emitters may be reflected straight back from the skin surface, resulting in oxygen saturation readings that are falsely low. Also, reflectance mode sensors inherently have a weaker detected signal and a correspondingly lower signal-to-noise ratio resulting in less accuracy than transmission mode sensors.

FIG. 4A illustrates the configuration of a transmission-mode pulse oximetry sensor attached to a fetal scalp. Emitters 360 and a detector 370 are longitudinally embedded within the fetal scalp 10, that is, in a plane parallel to the scalp surface 12. As with the reflectance mode sensor configuration described above, this sensor configuration also measures a relatively small tissue volume. Emitted light follows the paths 380 from the emitters 360 to the detector 370, illuminating only the tissue layers proximate the plane of the emitters 360 and the detector 370. Thus, deeper scalp layers cannot be measured without deeper insertion of the spiral probe and the accompanying risk of injury. Also, interfering light following a back-scattered path 382 from the scalp surface may be detected.

FIG. 4B illustrates another transmission mode sensor configuration. Emitters 360 are positioned against the scalp surface 12 and a detector 370 is embedded in the fetal scalp 10. In contrast to the sensor configurations of FIGS. 3 and 4A, the emitters 360 and detector 370 are transverse to the scalp, that is, in a plane perpendicular to the scalp surface 12. Thus, emitted light follows the paths 380 along tissue layers extending from the scalp surface 12 to the furthest extent of the detector 370. The cross-sectional area of the detector 370, however, is inherently limited to avoid excessive trauma to the scalp. As a result, the measured tissue volume, which is a function of the detector active area, is also limited.

The fetal pulse oximetry sensor according to the present invention addresses the above-stated problems inherent in conventional fetal oximetry sensors. Sensor configurations are described that measure a larger tissue volume or measure a deeper tissue layer in order to incorporate the larger arterioles and a larger blood fraction in the derivation of oxygen saturation. Also, methods are described for stimulating localized arterial flow to increase blood fraction and overcome the effects of localized oxygen consumption. Further, a method using an additional wavelength is described for detecting inadequate blood fraction.

One aspect of the invention is a sensor comprising a base and a probe having a first portion proximate the base and a second portion distal the base. The probe second portion has a light emitting region, and there is a light collecting region distal the light emitting region. The probe second portion is embeddable within a tissue site so that light transmitted from the emitting region is received at the light collecting region after passing through the tissue site.

In one embodiment, the light collecting region comprises a detector located proximate the base. Encapsulated within the base is a generally planar substrate having a first side proximate the probe and a second side distal the probe. The detector is mounted to the first side of the substrate and an emitter is mounted on the substrate proximate the probe first portion so that light is transmitted from the emitter and reflected within the probe to the light emitting region. In particular, the emitter is mounted on the substrate second side, and the probe first portion extends through the substrate from the first side to the emitter on the second side. The emitter may be flush mounted or end-mounted to the substrate second side. In this embodiment, the substrate also functions as a light shield between the emitter and the detector. Alternatively, the emitter is mounted on the substrate first side, and a light shield separates the emitter and the detector.

In another embodiment, a light collecting region is disposed in the second probe portion so that the light emitting region and the light collecting region are in a plane substantially parallel to the tissue site surface. The light collecting region and the light emitting region are angled relative to the plane of the light emitting and light collecting regions. In this manner, the sensor advantageously measures deeper tissue layers. A generally planar substrate is encapsulated within the base with a first side proximate the probe and a second side distal the probe. The detector and the emitter are mounted to the substrate proximate the probe first portion. In particular, the emitter and the detector are mounted on the same side of the substrate with a light shield separating the emitter and the detector. The detector and the emitter may be mounted to the substrate second side, with the probe first portion extending through the substrate from the first side to the second side so that light transmitted from the emitter is reflected within the probe to the light emitting region and light received at the light collecting region is reflected within the probe to the detector. The emitter and the detector may be generally flush-mounted to the substrate or end-mounted. The base further comprises a light absorbing material proximate the base surface that contacts the tissue site.

Another aspect of the present invention is a pulse oximetry sensor method comprising the steps of embedding an emitting region within a tissue site so that light from the emitting region illuminates the tissue site and positioning a detector proximate to the tissue site so as to receive light passing through the tissue site from the emitting region. A light collecting region of the detector is of substantially greater area than the emitting region. A larger collecting region outside the tissue site advantageously provides for the measurement of a larger tissue volume without increasing the area of the emitting region embedded within the tissue site, which would result in greater tissue damage when the sensor probe is inserted into the tissue site. The sensor method may also comprise transmitting light from an emitter located proximate the tissue site to the emitting region. The sensor method may further comprise shielding the detector from the emitter so that the detector substantially receives light only after passing through the tissue site. In addition, the sensor method may comprise heating the tissue site to stimulate the flow of arterial blood to the tissue site. Alternatively, arterial flow may be stimulated by applying a vasodilating substance to the tissue site.

Yet another aspect of the present invention is a pulse oximetry sensor method comprising the steps of embedding an emitting region within a tissue site so that light from the emitting region illuminates the site and also embedding a collecting region within the tissue site distal the emitting region so as to receive light passing through the tissue site from the emitting region. The emitting region and the collecting region are angled away from a surface of the tissue site. In this manner, measurements are obtained from the deeper layers of the tissue site. The sensor method may also comprise transmitting light from an emitter located proximate the tissue site to the emitting region and transmitting light to a detector located proximate the tissue site from the collecting region. The sensor method may further comprise absorbing light from the emitting region that is reflected from the surface of the tissue site so that substantially no reflected light is received at the collecting region. Also, the sensor method may comprise the additional step of shielding the detector from the emitter so that the detector substantially receives light only after passing through the tissue site.

A further aspect of the current invention is a pulse oximetry sensor method comprising measuring a first intensity ratio from a first pair of wavelengths illuminating a tissue site, and measuring a second intensity ratio from a second pair of wavelengths illuminating the tissue site. Applying a first calibration curve to the first intensity ratio yields a first saturation value. Similarly, applying a second calibration curve to the second intensity ratio yields a second saturation value. Detecting a low blood fraction condition at the tissue site is accomplished from an examination of the difference between the first saturation value and the second saturation value.

An additional aspect of the pulse oximetry sensor according to the present invention is an emitting means for illuminating a tissue site and a collecting means for receiving light from the emitting means after passing through the tissue site so as to measure characteristics of the tissue site. Further, there is a probe means for embedding at least a portion of the emitting means within the tissue site and for attaching the collecting means distal the emitting means. In one embodiment, the collecting means may comprise a detecting means attachable proximate the tissue site. Also the emitting means may comprise a light generating means attachable proximate the tissue site and a transmitting means for conveying light from the generating means to a light emitting region of the probe means. The sensor may also have a shielding means for blocking direct light between the light generating means and the detecting means. In another embodiment, the probe means may also comprise a means for embedding at least a portion of the collecting means within the tissue site. In this embodiment, there may be an angling means for measuring tissue layers distal said probe means. The sensor may also have a transmitting means for conveying light from a generating means to a light emitting region of the probe means and a receiving means for conveying light from a light collecting region of the probe means to a light detecting means attachable proximate the tissue site. There may also be an absorbing means for preventing light from reaching the light collecting region after reflection from the surface of the tissue site. Also included may be a shielding means for blocking direct light between the light generating means and the light detecting means.

BRIEF DESCRIPTION OF THE DRAWINGS

The present invention will be described in detail below in connection with the following drawing figures in which.

DETAILED DESCRIPTION OF THE PREFERRED EMBODIMENTS

Figure 1:
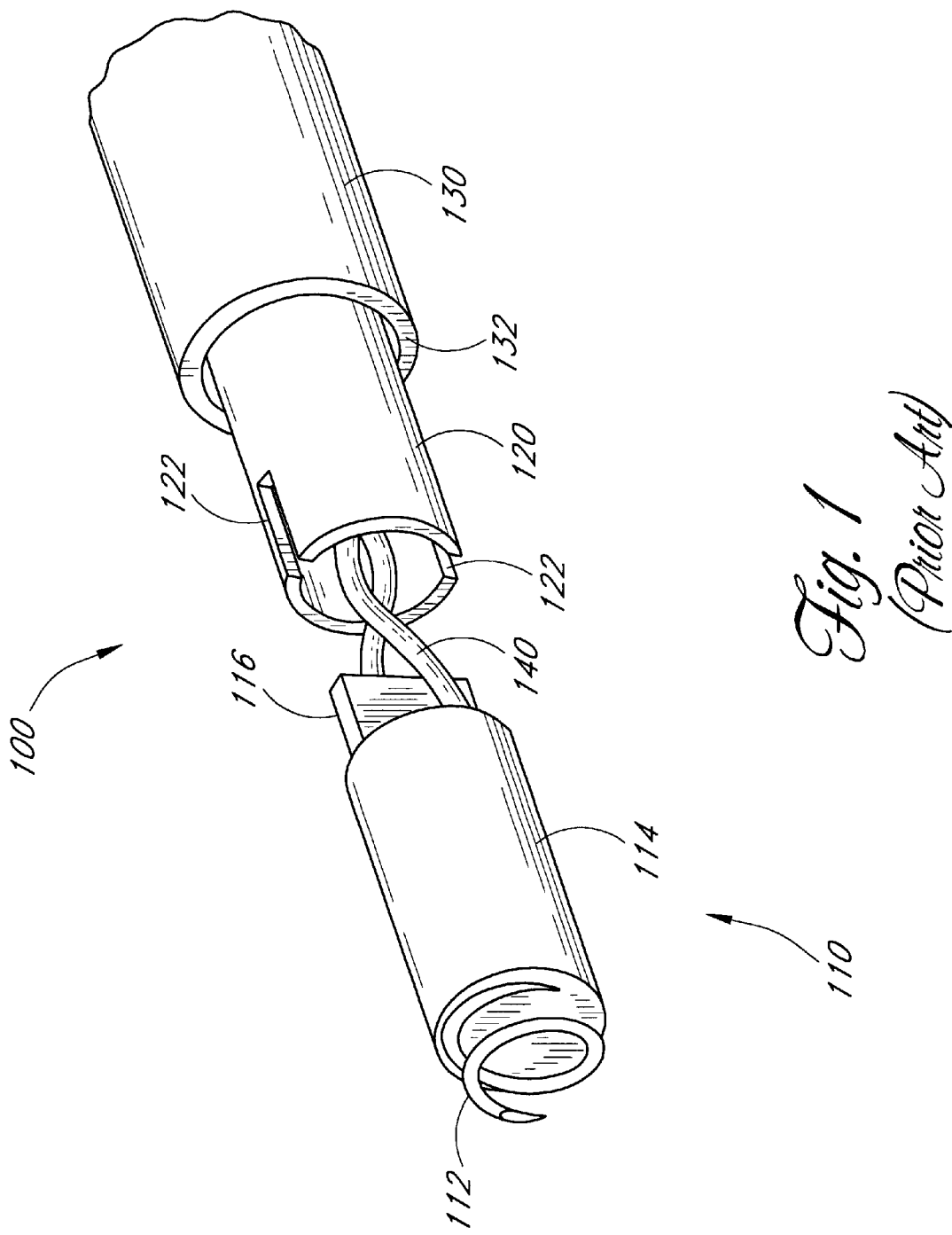
FIG. 1 is an illustration of a prior art fetal ECG sensor having a spiral probe for attachment to the fetal scalp.
Figure 5:
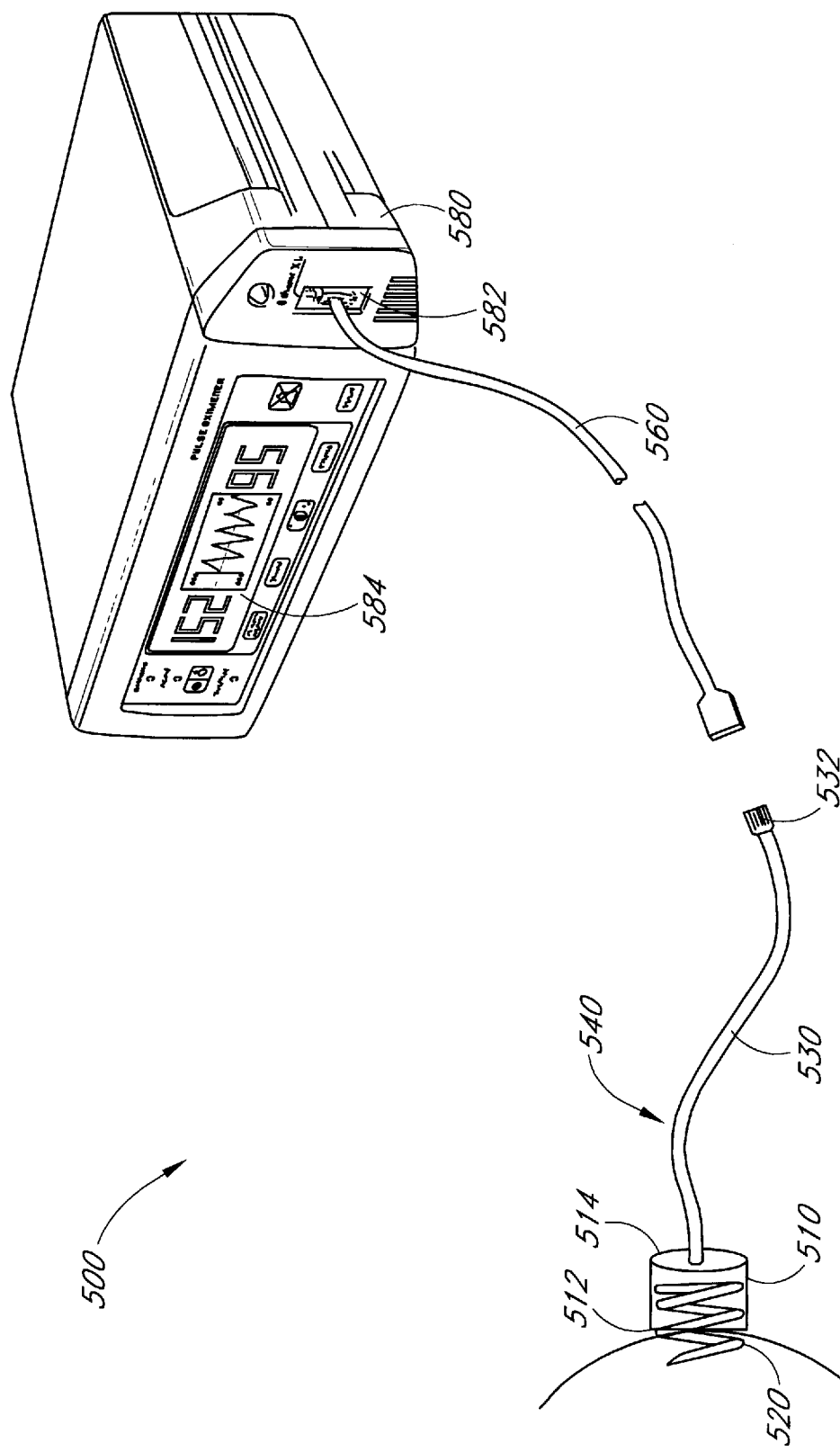
FIG. 5 is an illustration of a fetal pulse oximetry system, depicting the fetal sensor, patient cable and monitor.

FIG. 5 illustrates a fetal pulse oximetry system 500. The system 500 includes a fetal sensor 540, a patient cable 560 and a pulse oximetry monitor 580. The fetal sensor 540 includes a sensor base 510, a spiral probe 520, and a pigtail 530. The spiral probe 520 is attached to a front end 512 of the sensor base 510 and extends away from the base 510. The pigtail 530 is connected to a backend 514 of the sensor base 510 at one end and extends from the sensor base 510 to a position external to the mother, terminating in a patient cable connector 532. The probe 520 attaches to the fetal scalp as described above with respect to FIG. 1. That is, the probe 520 is screwed into the presenting portion of fetus, specifically the fetal scalp 10. The patient cable 560 connects to the pigtail 530 at one end and to the monitor 580 at the other end and transmits signals between the monitor 580 and the sensor 540. The monitor 580 has a connector 582 for receiving one end of the patient cable 560. The monitor 580 controls the sensor 540 and processes intensity signals from the sensor 540, providing a display 584 of the resulting oxygen saturation, pulse rate and plethysmograph.

Figure 6:
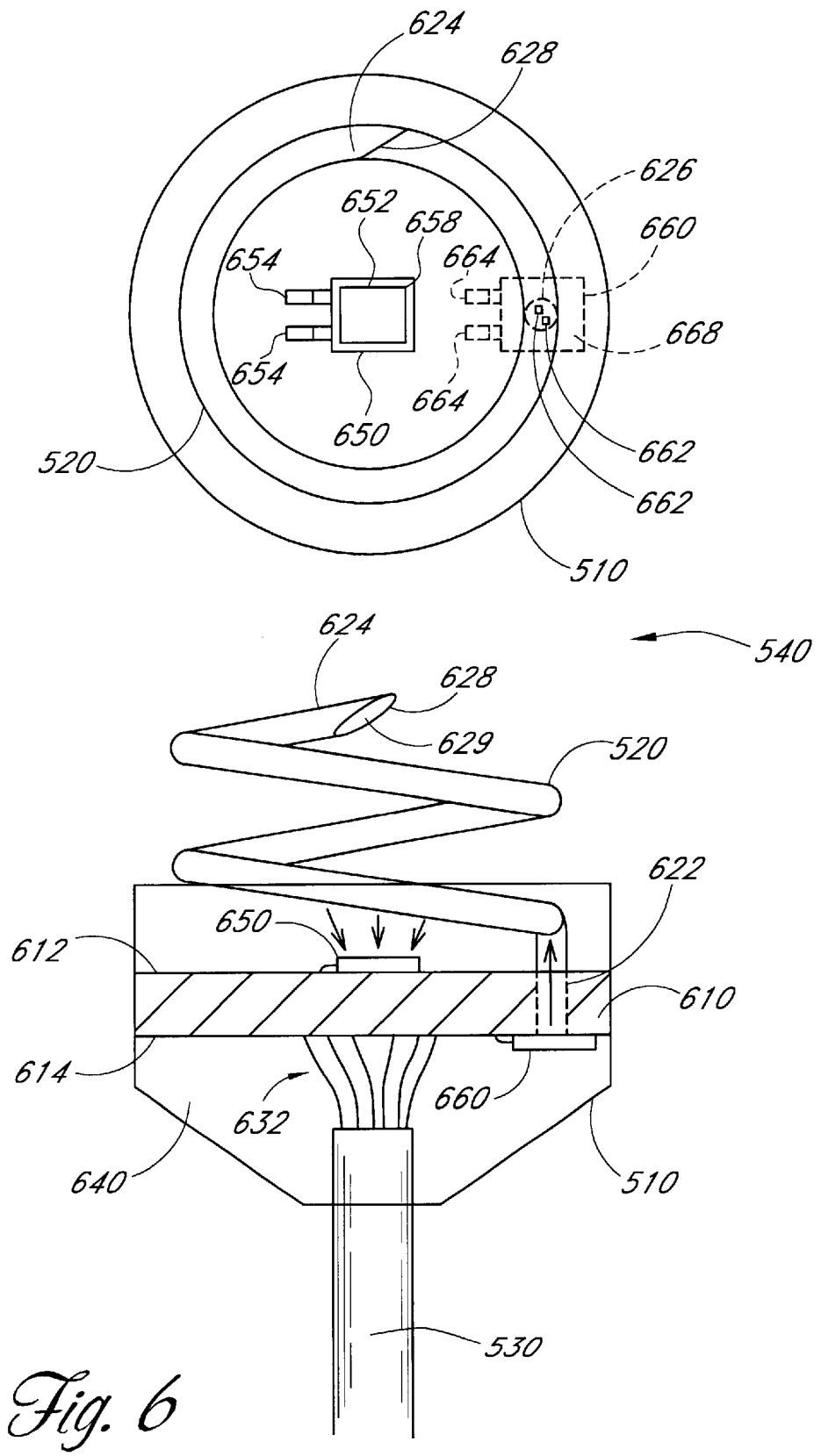
FIG. 6 is a cross-sectional view depicting one embodiment of a fetal pulse oximetry sensor according to the present invention, illustrating an emitter flush-mounted to the backside of a base substrate.

FIG. 6 illustrates one embodiment of the fetal pulse oximetry sensor 540. The sensor 540 has a sensor base 510, probe 520 and pigtail 530 as described above. The sensor base 510 is constructed of a substrate 610 encased in an encapsulant 640. The substrate 610 has a first side 612 facing the probe 520 and a second side 614 facing the pigtail 530. One end of the pigtail 530 is attached to the second side 614 of the substrate. Individual conductors 632 of the pigtail 530 are electrically connected to the substrate, providing electrical communication between these conductors and the components on the first side 612, through "vias," and the second side 614 of the substrate. The pigtail 530 is partially encapsulated, further securing it to the substrate 610 and sensor base 510.

A detector package 650 is mounted on the first side 612 of the substrate 610 and an emitter package 660 is mounted on the second side 614 of the substrate 610. The detector package 650 contains a photodiode detector chip 652 mounted to leads 654 and enclosed in an encapsulant 658. The detector package is mounted so that the active, light collecting region of the photodiode 652 faces the probe 520 and detects light from the direction shown by the arrows. The detector package leads 654 are electrically connected to the substrate 610. The emitter package 660 contains a pair of light emitting diodes (LEDs) 662 encased in an encapsulant 668, one of which emits a narrow band of red wavelength light and the other of which emits a narrow band of infrared wavelength light. The LEDs 662 are connected back-to-back and in parallel with the emitter package leads 664. The emitter package 660 is mounted so that the active regions of the LEDs 662 face into the substrate 610, generating light into the probe 520 in the direction shown by the arrow. The emitter package leads 664 are electrically connected to the substrate 610. The detector package 650 and emitter package 660 are advantageously mounted on opposite sides 612, 614 of the substrate 610 so that the substrate 610 also functions as a light shield. This prevents light leaking from the LEDs 662 from directly reaching the photodiode 652 without first passing through perfused tissue.

The probe 520 is hollow and constructed of a highly reflective material, such as stainless steel. One probe end 622 is mounted through the substrate 610 so that the inner diameter 626 of the probe 520 encompasses both of the LEDs 662. The probe 520 is partially encapsulated, further securing it to the substrate 610 and the sensor base 510. So constructed, the LEDs 662 can transmit light into the hollow portion of the probe 520. This light is then transmitted through the substrate 610 and reflected around the probe spirals and out the other probe end 624. This probe end 624 is cut at an oblique angle, forming a sharp tip 628, which can easily penetrate fetal scalp tissue. The cut is also made to form an opening 629 facing generally downward and toward the center portion of the substrate 610 where the detector package 650 is located. The probe opening 629 is sealed with a material, such as an epoxy, that is transparent to the red and infrared LED wavelengths. In this manner, light from the LEDs 662 is transmitted through the opening 629 and yet tissue is prevented from accumulating within the hollow probe portion proximate the opening 629. Thus, the opening 629 is a light emitting region of the probe 520.

Figure 3:
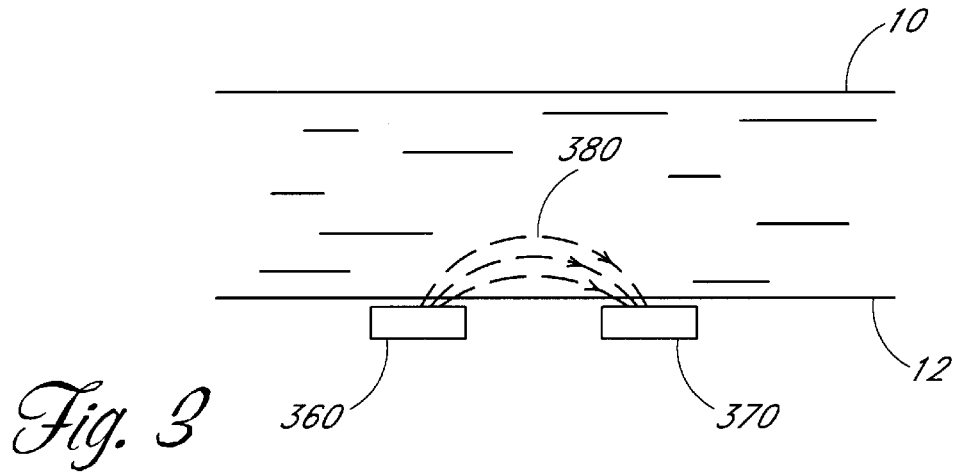
FIG. 3 is a cross-sectional depiction of a reflectance mode, pulse oximetry sensor attached to the surface of a fetal scalp.
Figure 4A:
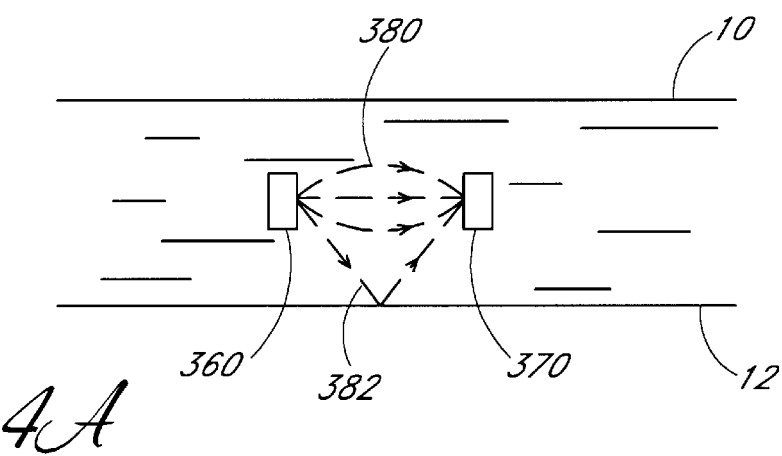
FIG. 4A is a cross-sectional depiction of a transmission mode, pulse oximetry sensor located within the tissue of a fetal scalp and longitudinally-oriented with respect to the scalp surface.
Figure 4B:
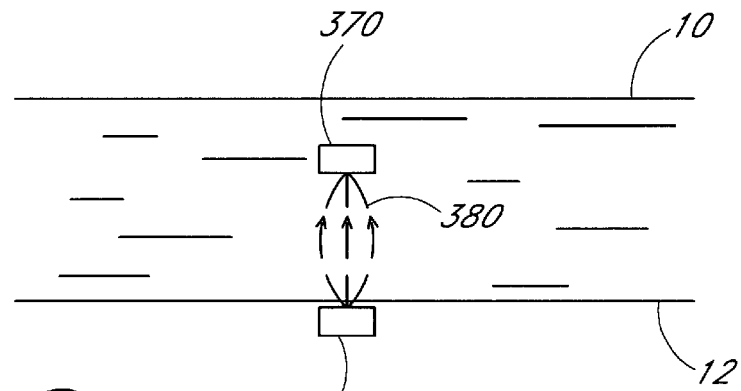
FIG. 4B is a cross-sectional depiction of a transmission mode pulse oximetry sensor, transversely-oriented with respect to the scalp surface, where the detector is located within the tissue of a fetal scalp and the emitters are attached to the surface of the scalp.
Figure 7:
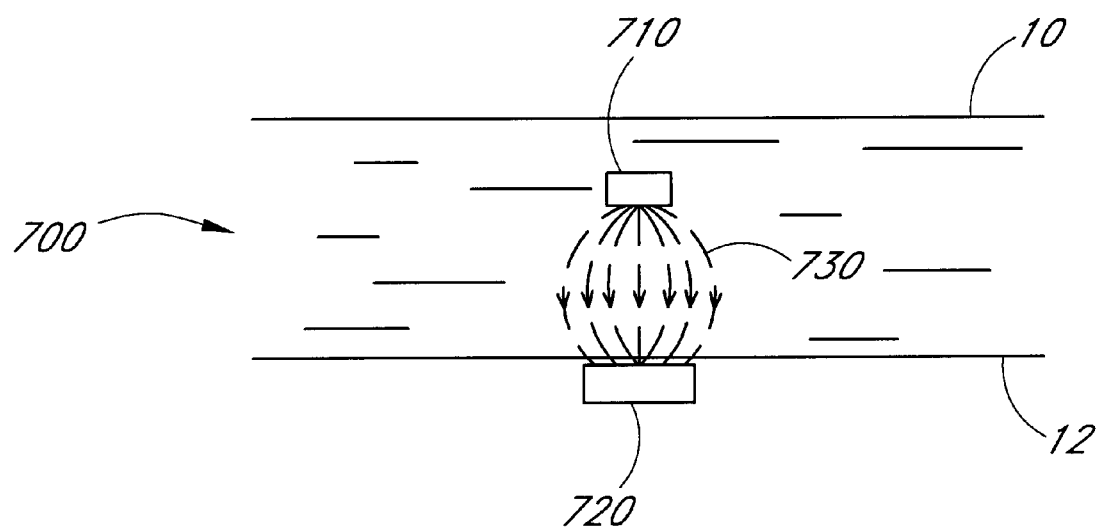
FIG. 7 is a cross-sectional depiction of the fetal pulse oximetry sensor of FIG. 6, illustrating a transverse orientation to the fetal scalp, an emitting region located within the tissue of a fetal scalp, and a detector attached to the surface of the scalp.

FIG. 7 depicts a sensor configuration 700 corresponding to the sensor 540 (FIG. 6) described above. Specifically, with the sensor 540 (FIG. 6) attached to a fetal scalp, the detector 650 (FIG. 6) is positioned such that a light detecting region 720 is located at the scalp surface 12. Also, the probe opening 629 (FIG. 6) is positioned such that a light emitting region 710 is located within the scalp 10. Light transmitted from the emitting region 710 follows the paths 730 to the detecting region, measuring a relatively large tissue volume compared to the sensor configurations depicted in FIGS. 3, 4A and 4B. In particular, the sensor 700 is a transmission-mode configuration not unlike the adult fingertip sensors and in stark contrast to the reflectance-mode configuration depicted in FIG. 3. Also, the detecting region 720 is located outside the scalp 10 in contrast to the longitudinal configuration of FIG. 4A and the transverse configuration of FIG. 4B each having an embedded detector. Thus, the cross-section area of the light detecting region 720 is unconstrained by considerations of tissue trama, advantageously allowing the detecting region 720 to collect light transmitted through a relatively large tissue volume.

Figure 8:
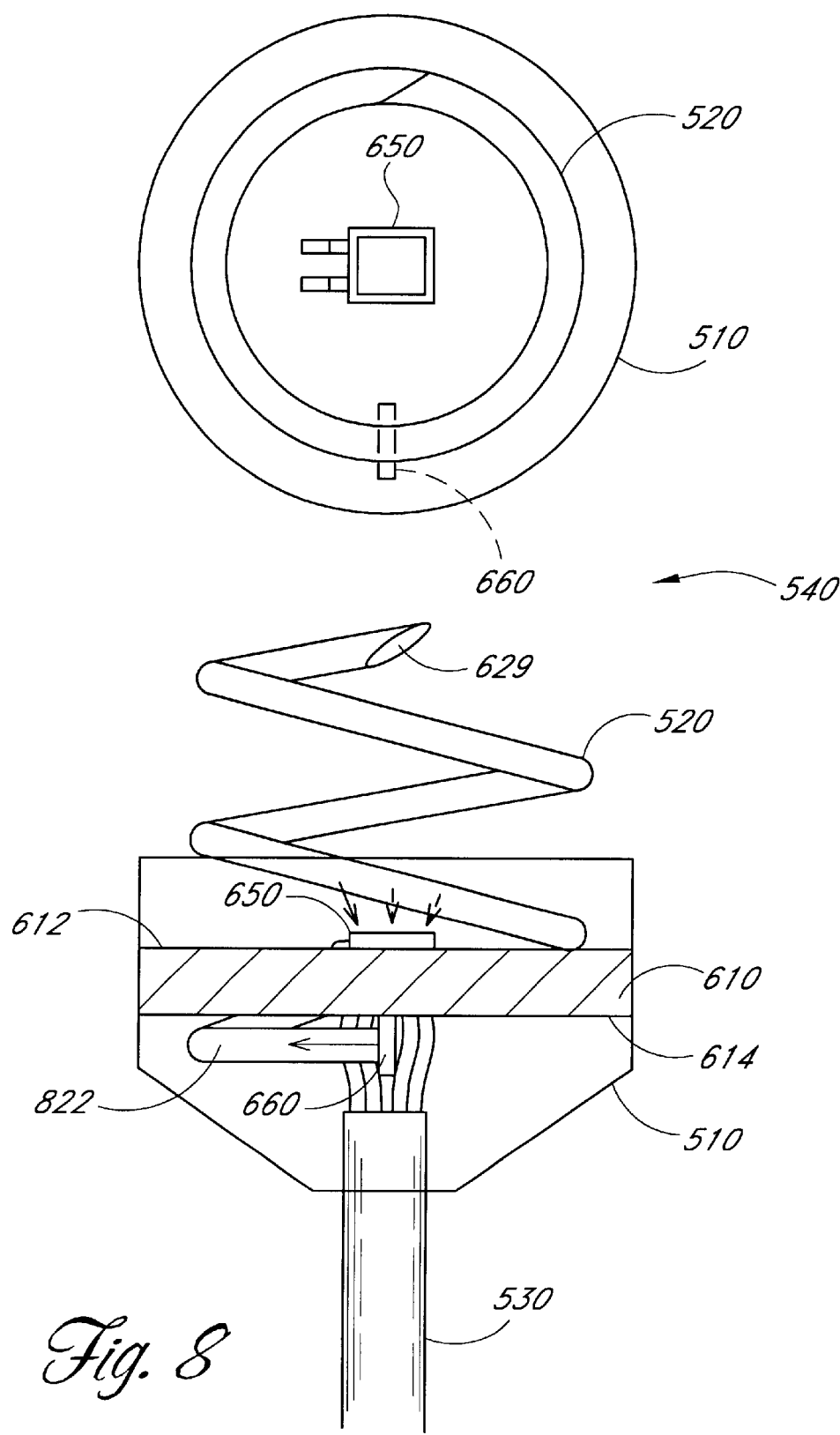
FIG. 8 is a cross-sectional view of another embodiment of a fetal pulse oximetry sensor, illustrating an emitter edge-mounted to a base substrate.

FIG. 8 depicts an alternative embodiment to the sensor depicted in FIG. 6. By comparison, this sensor 540 has a sensor base 510, probe 520 and pigtail 530. The pigtail 530 is as described above. The sensor base 510 is constructed of a substrate 610 encased in an encapsulant 640, also as previously described. A detector package 650 is mounted on the first side 612 of the substrate 610 and an emitter package 660 is mounted on the second side 614 of the substrate 610, as previously described. By contrast, however, the emitter package 660 is end-mounted to the second side 614 of the substrate 610. Further, one end portion 822 of the probe 520 spirals through the substrate 610 so that the inner diameter 626 of the probe 520 encompasses both of the LEDs 662 (FIG. 6). The remainder of the probe 510 is as described above with respect to FIG. 6.

Figure 9:
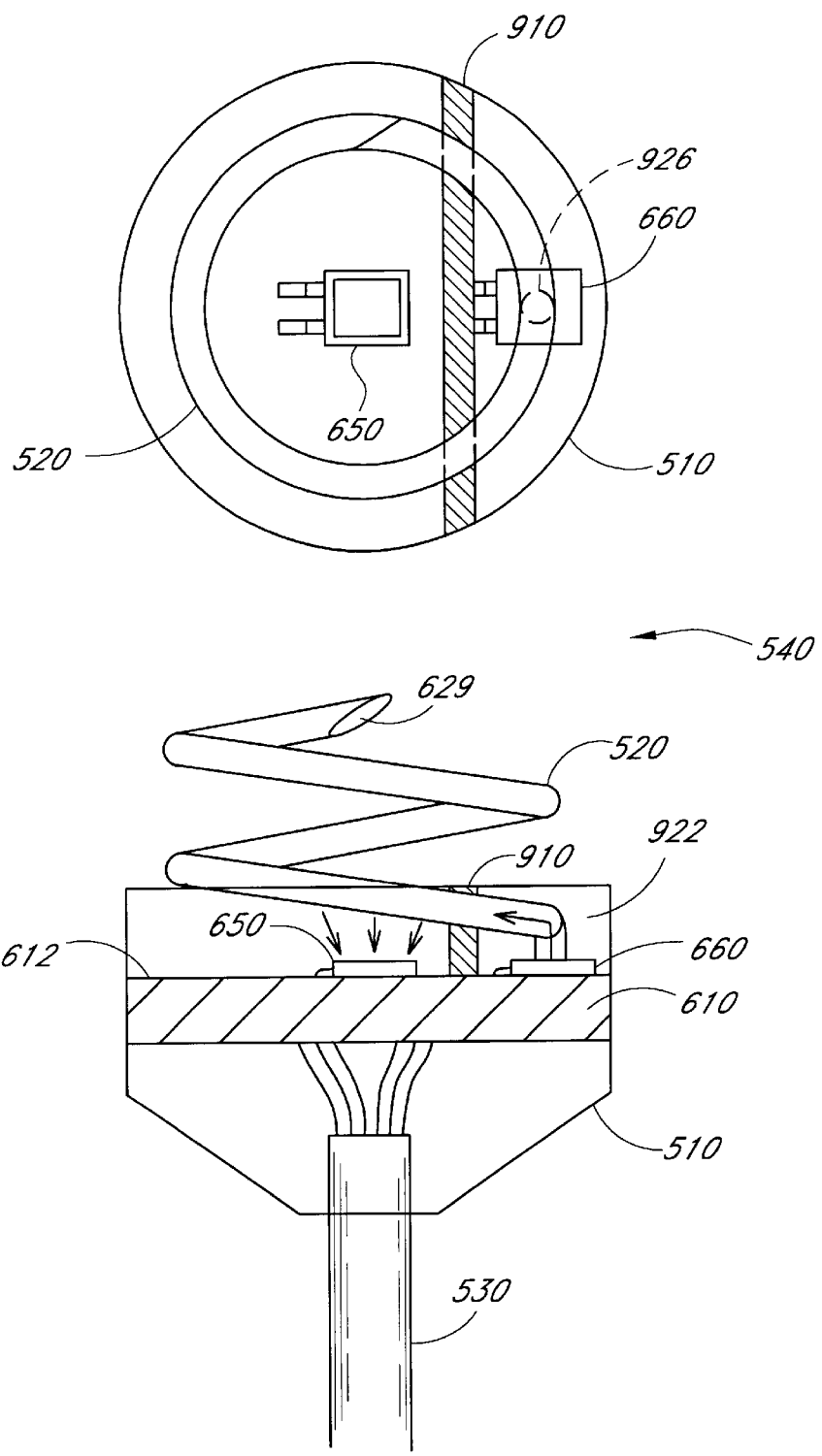
FIG. 9 is a cross-sectional view of yet another embodiment of a fetal pulse oximetry sensor, illustrating a detector and emitters co-located on the probe side of a base substrate.

FIG. 9 depicts another alternative embodiment to the sensor depicted in FIG. 6. Again, this sensor 540 has a sensor base 510, probe 520 and pigtail 530. The pigtail 530 is as described above. The sensor base 510 is constructed of a substrate 610 encased in an encapsulant 640, also previously described. By contrast with the embodiments described above, the detector package 650 and the emitter package 660 are mounted on the first side 612 of the substrate 610. Because the substrate 610 does not separate the LEDs from the photodiode, a light barrier 910 is installed between the emitter package 660 and detector package 650. The emitter package 660 is mounted so that the active regions of the LEDs 662 face away from the substrate 610. One probe end 922 is mounted adjacent the emitter package 660 so that the inner diameter 626 of the probe 520 encompasses both of the LEDs 662 (FIG. 6). The remainder of the probe 510 is as described above with respect to FIG. 6.

Figure 10A:
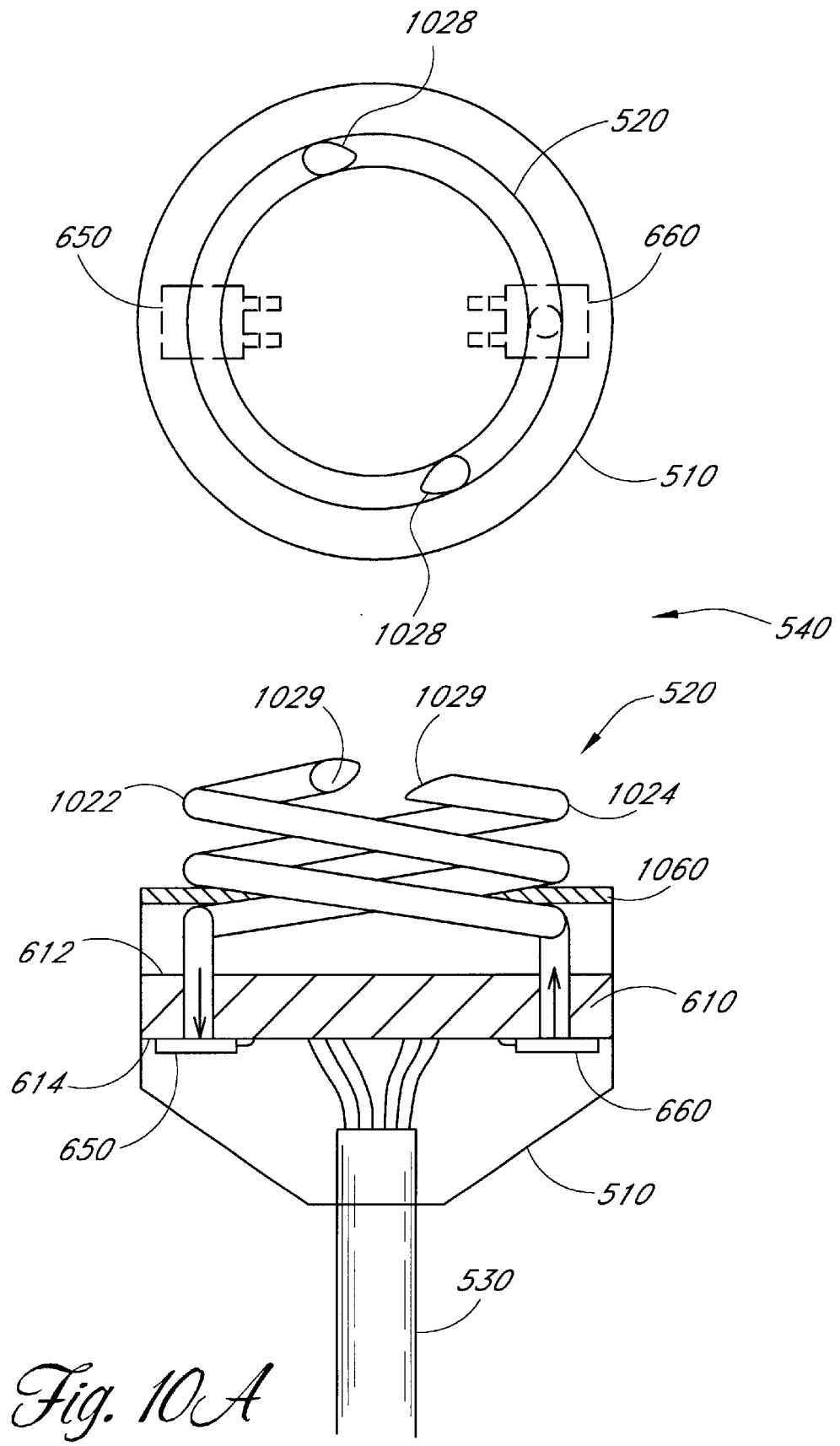
FIG. 10A is a cross-sectional view of another embodiment of a fetal pulse oximetry sensor, illustrating a probe having twin spiral needles with angled light emitting and detecting openings at the probe tip.

FIG. 10A illustrates another embodiment of the fetal pulse oximetry sensor 540. The sensor 540 has a sensor base 510, probe 520 and pigtail 530. The pigtail 530 is as described above. The sensor base 510 is constructed of a substrate 610 having a first side 612 and a second side 614, also as described above. A detector package 650 and an emitter package 660, described above, are mounted on the second side 614 of the substrate. The probe 520, however, is distinct from the embodiments described above.

The probe 520 is constructed of two hollow spiral needles 1022, 1024 of highly reflective material. At one end of the probe 510, each needle 1022, 1024 is mounted through the substrate 610. A first needle 1022 is terminated at the detector package 650. A second needle 1024 is terminated at the emitter package 660 so that its inner diameter 1026 encompasses both of the LEDs 662 (FIG. 6). At the other end of the probe 510, each needle 1022, 1024 is cut at an oblique angle, forming sharp tips 1028, which can easily penetrate fetal scalp tissue. The needles are also cut to form openings 1029 facing generally inward and upward at an angle to the sensor base 510. The opening 1029 at the end of the first needle 1022 creates a light-detecting region. The opening 1029 at the end of the second needle 1024 creates a light-emitting region. The probe openings 1029 are sealed as described above. A light absorbing material 1060 covers the face of the sensor base 510 proximate the probe 520 to prevent photons emitted at one opening 1029 from being reflected off the base 510 and detected at the other opening 1029.

Figure 10B:
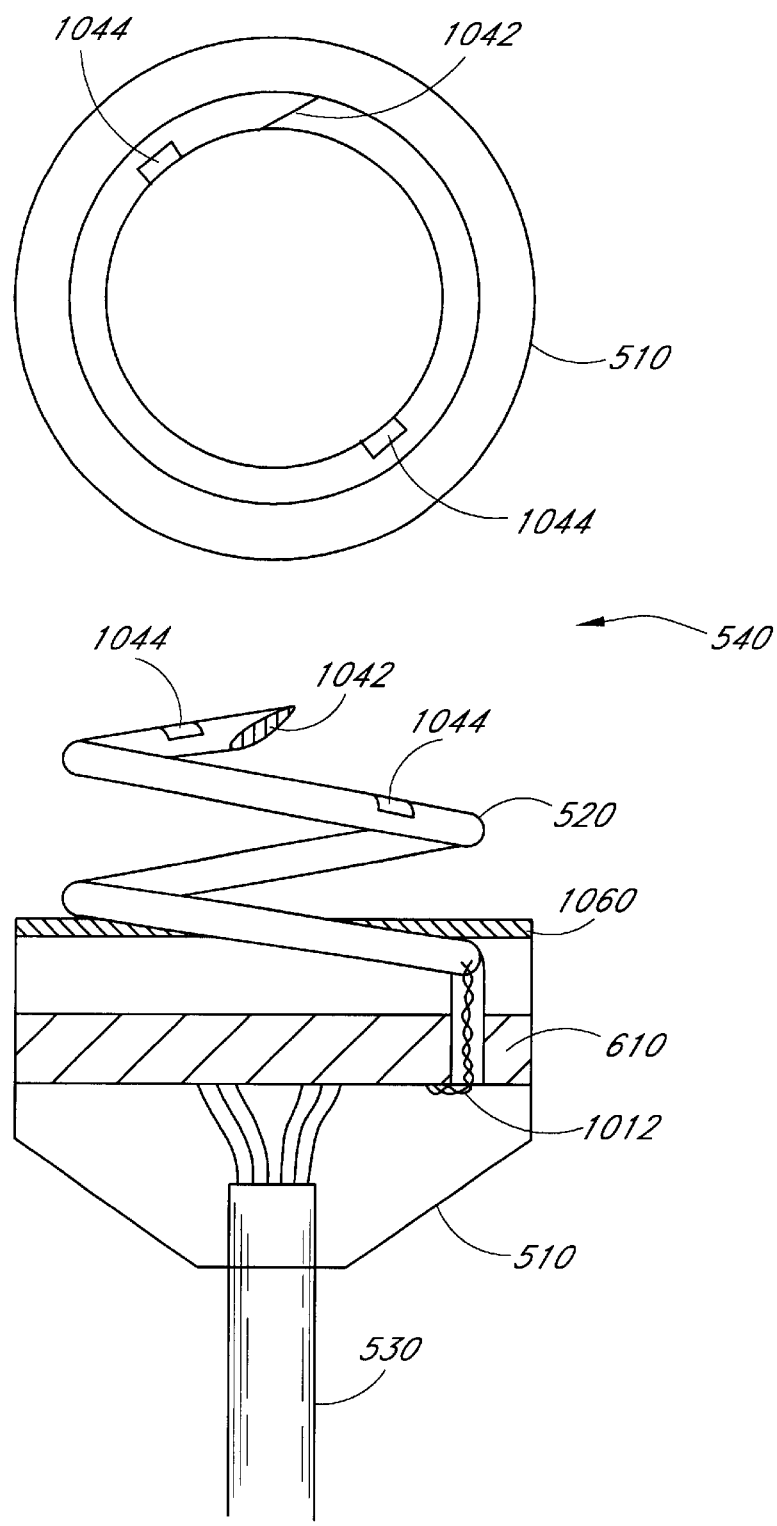
FIG. 10B is a cross-sectional view of a further embodiment of a fetal pulse oximetry sensor, illustrating a probe containing emitters and a detector mounted in the probe adjacent angled slots located along the probe.

FIG. 10B illustrates yet another embodiment of the fetal pulse oximetry sensor 540. The sensor 540 has a sensor base 510, probe 520 and pigtail 530 as described above with respect to FIG. 5. The probe 510 comprises a single, hollow spiral needle. The probe end 1042 is solid and cut at an oblique angle, forming a sharp solid tip, which can easily penetrate fetal scalp tissue. A pair of slots 1044 form openings along the probe. The slots 1044 are located proximate the probe end 1042 and on opposite portions of one loop of the probe spiral. The slots 1044 are oriented to face generally inward and upward at an angle to the sensor base 510. Mounted inside the probe 510 proximate the slots 1044 are LED chips and a photodiode chip (not shown). The LEDs are mounted so as to transmit light through one of the slots 1044, creating a light-emitting region at that slot 1044.

The photodiode is mounted so as to collect light through the other one of the slots 1044, creating a light-detecting region at that slot 1044. A light absorbing material 1060 covers the face of the sensor base 510 proximate the probe 520 to prevent photons emitted at one slot 1044 from being reflected off the base 510 and detected at the other slot 1044. The LEDs and photodiode are connected to the substrate 610 via conductors 1012 threaded through the hollow portion of the probe 520 allowing drive current from the pulse oximetry monitor 580 (FIG. 5) to activate the LED chips via the pigtail 530. Similarly, an intensity signal detected by the photodiode chip is received by the pulse oximetry monitor 580 (FIG. 5) via the pigtail 530.

Figure 11:
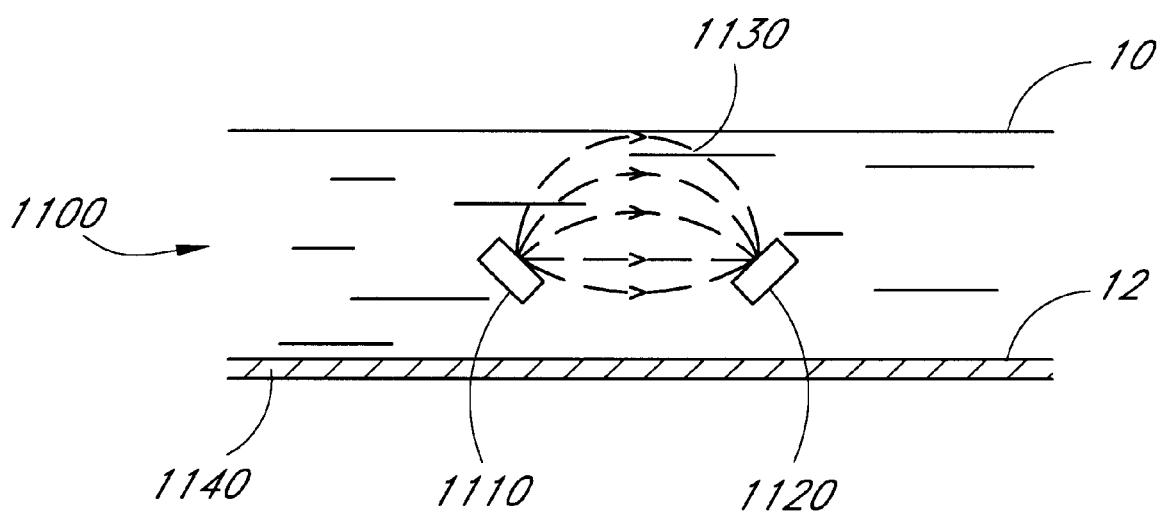
FIG. 11 is a cross-sectional depiction of the pulse oximetry sensor of FIGS. 10A and 10B, illustrating emitting and detecting regions located within the tissue of the fetal scalp and obliquely-oriented to the scalp surface.

FIG. 11 depicts a sensor configuration 1100 corresponding to the sensor 540 described above in FIGS. 10A and 10B. Specifically, with the sensor 540 (FIGS. 10A–B) attached to a fetal scalp, the probe openings 629 (FIG. 10A) or probe slots 1044 (FIG. 10B) are positioned such that a light emitting region 1110 and light collecting region 1120 are located within the scalp 10. Light transmitted from the emitting region 1110 follows the paths 1130 to the detecting region 1120, advantageously measuring a relatively large tissue volume and deeper tissue layers compared to the sensor configurations depicted in FIGS. 3, 4A, 4B. In particular, the sensor 1100 is a transmission-mode configuration not unlike the adult fingertip sensors and in stark contrast to the reflectance-mode configuration depicted in FIG. 3. Also, the angled emitting region 1110 and detecting region 1120 advantageously allow the detecting region 720 to collect light transmitted through a relatively larger and deeper tissue volume than the strictly longitudinal or transverse configuration of FIGS. 4A and 4B respectively. Further, the absorbing layer 1140 avoids the backscattering interference depicted in FIG. 4A.

One of ordinary skill will appreciate that there are many variations in the sensors of FIGS. 6, 8, 9, 10A and 10B within the scope of this invention. The light emitting region 629 of FIGS. 6, 8 and 9 can be at a slot along a hollow probe that transmits light reflected inside the probe from emitters located external to the probe. As an alternative, the light emitting region 629 may be the end of a fiber optic located at a probe opening at the probe tip or a slot along the probe, where the fiber optic is mounted inside the probe and transmits light from emitters located external to the probe and coupled to the fiber optic. As another alternative, the light emitting region 629 may be emitters mounted inside a probe, with the surface of the emitters located at a probe opening at the probe tip or a slot along the probe. Conductors located inside the probe electrically connect the emitters to emitter drivers, which are located external to the probe.

The light emitting and detecting regions 1029 of FIG. 10A may be fiber optics having ends located at a probe opening at the tip or at slots along the probe, which transmit light between fiber optic ends and a detector or emitters located external to the probe. Further, the probe 520 of FIG. 10A may comprise a single needle 1022 having multiple openings located at or near the needle tip 1028 or elsewhere along the length of the needle 1022, with the detecting region and emitting region located at these openings. As described above, the detecting and emitting regions of such a single needle may be openings that transmit or receive light reflected inside a hollow needle, the ends of fiber optics that transmit or receive light, or the light sensitive surface of a needle-mounted detector and the light transmitting surfaces of needle-mounted emitters.

One of ordinary skill will also appreciate that the substrate 610 and pigtail 530 of FIGS. 6, 8, 9, 10A, and 10B may also be constructed in a variety of ways. The substrate 610 may be made of any number of materials suitable for mounting conductive traces and electronic components, such as standard circuit board material or ceramics with individually mounted components. Alternatively, the substrate may be an integrated circuit or a hybrid circuit. The pigtail 530 may be, for example, a cable of individual conductors or a flex circuit.

Figure 2A:
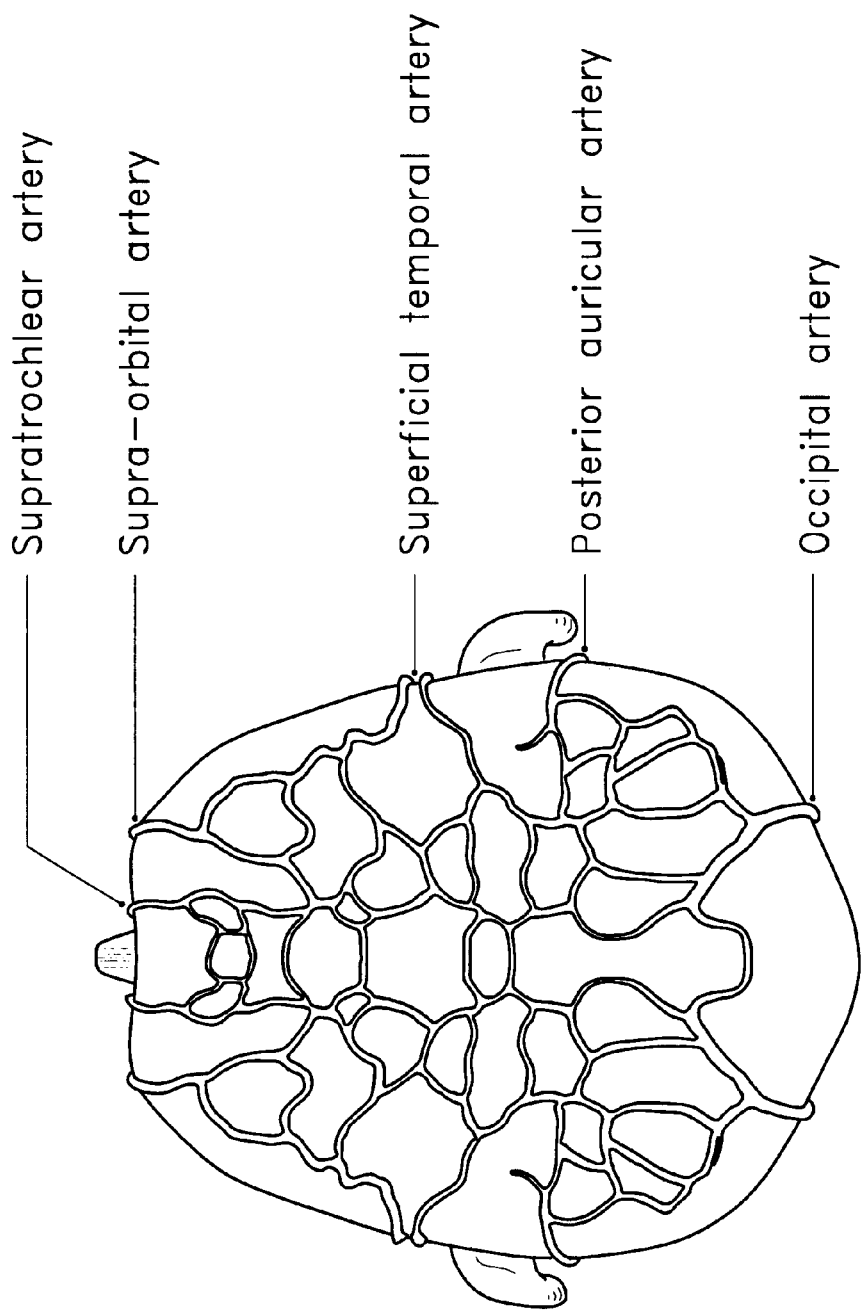
FIG. 2A is an illustration depicting the location of the larger arteries of the scalp.
Figure 2B:
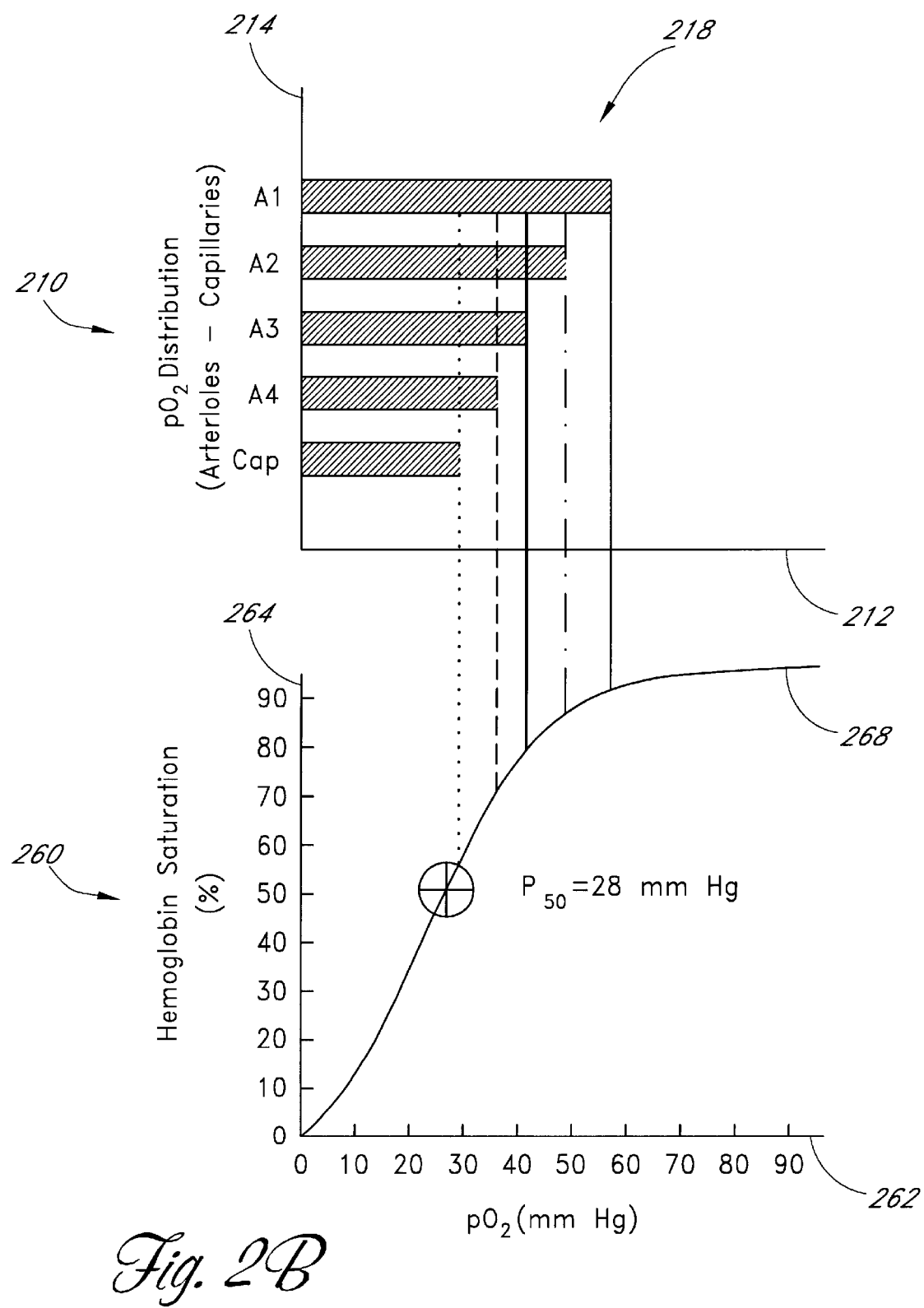
FIG. 2B is a graph of oxygen saturation as a function of arteriolar size and type.
Figure 2C:
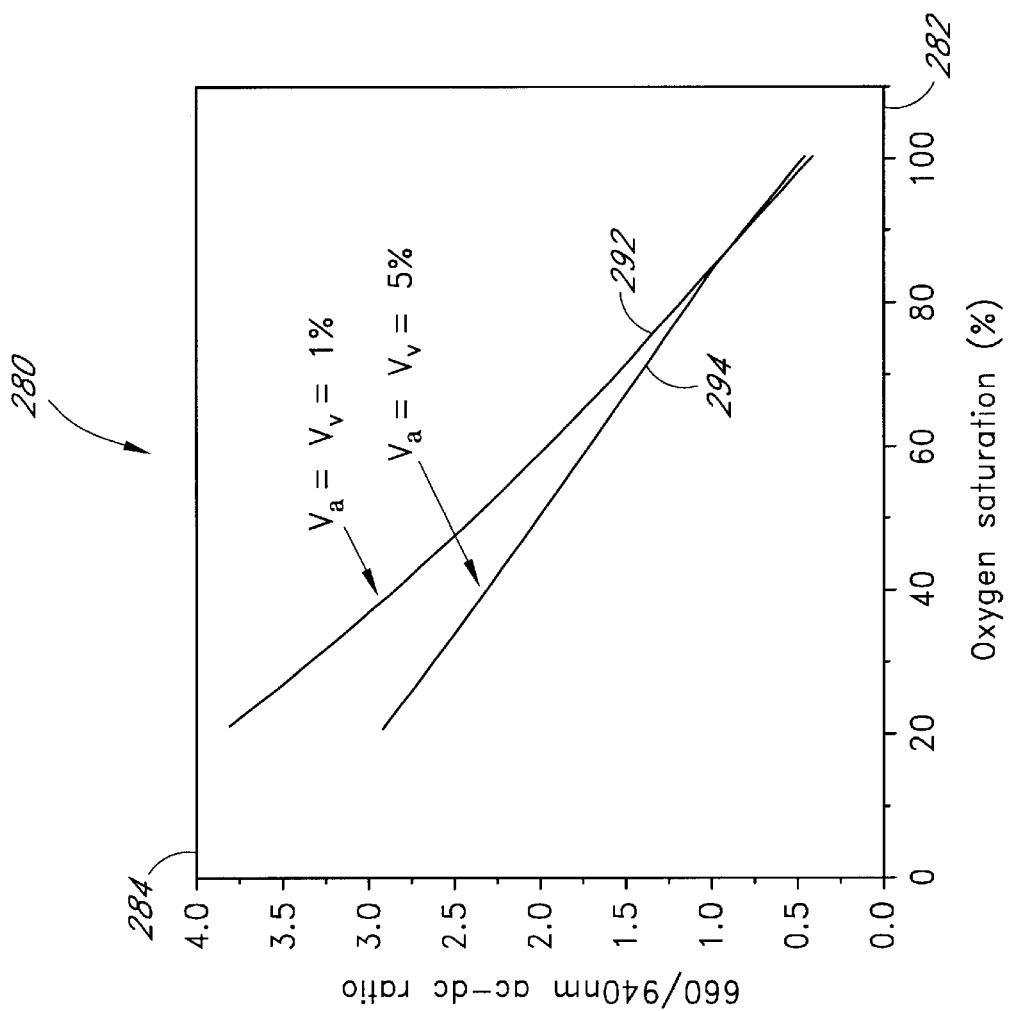
FIG. 2C is a graph of pulse oximetry calibration curves as a function of blood fraction.
Figure 12:
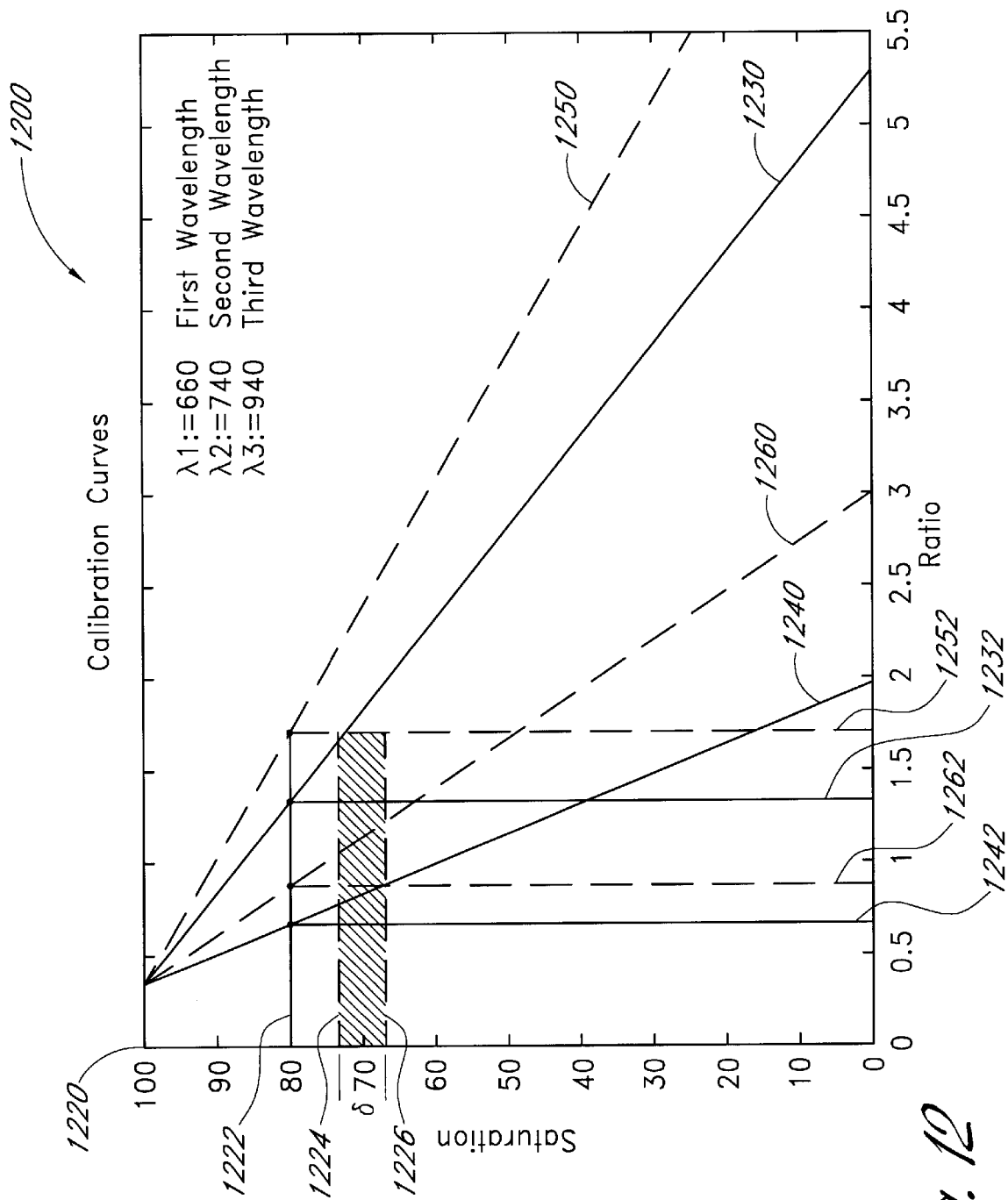
FIG. 12 is a graph depicting calibration curves for two pairs of wavelengths.

FIG. 12 shows a graph 1200 that illustrates detection of inadequate blood fraction using an additional wavelength. The graph 1200 has an x-axis 1210 corresponding to the measured ratio, R, and a y-axis 1220 corresponding to oxygen saturation. A first calibration curve 1230 corresponds to the measured signals at a first red wavelength, $\lambda 1$, and an infrared wavelength, $\lambda 3$. A second calibration curve 1240 corresponds to the measured signals at a second red wavelength, $\lambda 2$, and the infrared wavelength, $\lambda 3$. A first actual curve 1250 corresponds to a shift in the first calibration curve due to reduced blood fraction, as depicted in FIG. 2C. A second actual curve 1260 corresponds to a shift in the second calibration curve, also due to reduced blood fraction.

As shown FIG. 12, if the tissue site has a blood fraction corresponding to the "average" physiological conditions for which the first calibration curve and the second calibration curve were derived, then measurements made at wavelengths $\lambda 1$ and $\lambda 3$ should match measurements made at wavelengths $\lambda 2$ and $\lambda 3$. For example, if the first and second calibration curves 1230, 1240 are valid, a saturation reading 1222 of 80% would be indicated by a measured ratio 1232 at $\lambda 1$ and $\lambda 3$ of about 1.35 and a measured ratio 1242 at $\lambda 2$ and $\lambda 3$ of about 0.65. That is, measurements taken at either set of wavelengths would yield the same oxygen saturation reading.

By contrast, a low blood fraction condition would result in a shift in the actual relationships between $Sp_aO_2$ and R from the calibration curves 1230, 1240 to the actual curves 1250, 1260, as indicated by FIG. 2C above. Thus, a saturation value 1222 of 80% would result in a measured ratio 1252 of about 1.75 at $\lambda 1$ and $\lambda 3$ and a measured ratio 1262 of about 0.8 at $\lambda 2$ and $\lambda 3$. However, the calibration curves 1230, 1240 would translate these ratio measurements into a saturation reading 1224 of 73% at $\lambda 1$ and $\lambda 3$ and a saturation reading 1226 of 67% at $\lambda 2$ and $\lambda 3$. Because these saturation readings 1224, 1226 must be approximately the same for either set of wavelengths, the pulse oximeter would interpret this discrepancy $\delta$ (shaded) as an indication that blood fraction conditions are such that the stored calibration curves are invalid, resulting in erroneously low saturation readings. Therefore, the pulse oximeter would effectively detect a low blood fraction condition.

Localized arteriolar flow can also be stimulated to avoid a localized measurement of oxygen saturation and to increase the measured blood fraction. Hyperemia, or the increased flow of arterial blood to the capillaries, is effected by causing the opening of precapillary sphincters localized to the tissue proximate the fetal sensor. In one embodiment, the sensor body 510 (FIG. 5) and probe 520 (FIG. 5) are heated to a range between 40° C. and 43° C. The heating is accomplished with a thermistor mounted to the substrate 610 (FIG. 6). The thermistor current is supplied from the monitor 580 (FIG. 5) via the pigtail 530 (FIG. 5) and patient cable 560 (FIG. 5). The thermistor voltage is monitored by the monitor, also via the pigtail and patient cable. The monitor adjusts the heat generated by the thermistor by regulating the thermistor supply current. The sensor heat is measured by the monitor from the thermistor resistance, which is simply related to the supplied current and the measured voltage by Ohm's law. The characteristics of this thermistor feedback control loop, such as stability and response time, are determined by the control processor within the monitor.

In another embodiment, localized precapillary sphincters are opened by the topical application of vasodilating substances, such as thurfyl nicotinate or histamine iontophoresis. For example, just prior to the insertion of the sensor 540 (FIG. 5) in the birth canal for scalp attachment, the probe 520 (FIG. 5) is dipped in a solution of nicotinic acid.

The fetal pulse oximetry sensor has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A sensor comprising:

a base;

a probe having a first portion proximate said base and a second portion distal said base, said probe second portion embeddable within a tissue site;

a light emitting region of said probe second portion;

a light collecting region comprising a detector located proximate said base and spaced from said light emitting region;

a generally planar substrate encapsulated within said base, said substrate having a first side and a second side, said detector mounted to said substrate first side; and an emitter mounted on said substrate proximate said probe first portion so that light is transmitted from said emitter and reflected within said probe to said light emitting region, wherein said emitter is mounted on said substrate second side and said probe first portion extends through said substrate from said first side to said emitter on said second side whereby light transmitted from said emitting region is received at said light collecting region after passing through said tissue site.

2. The sensor of claim 1 wherein said emitter is mounted generally flush to said substrate second side.

3. The sensor of claim 1 wherein said emitter is end-mounted to said substrate second side.

4. The sensor of claim 1 further comprising a controllable heat generating element proximate said probe first portion.

5. The sensor of claim 1 wherein at least a portion of said probe is coated with a vasodilating substance.

6. A sensor comprising:

a base;

a probe having a first portion proximate said base and a second portion distal said base;

a light emitting region of said probe second portion;

a light collecting region spaced from said light emitting region, said light collecting region comprising a detector located proximate said base, said probe second portion embeddable within a tissue site so that light transmitted from said emitting region is received at said light collecting region after passing through said tissue site;

a generally planar substrate encapsulated within said base, said substrate having a first side and a second side, said detector mounted to said substrate first side;

an emitter mounted on said substrate first side so that light is transmitted from said emitter and reflected within said probe to said light emitting region; and a light shield separating said emitter and said detector.

7. A sensor comprising:

a base;

a probe having a first portion proximate said base and a second portion distal said base embeddable within a tissue site;

a light emitting region of said probe second portion; and a light collecting region disposed in said second probe portion and spaced from said light emitting region, so that said light emitting region and said light collecting region are in a plane substantially parallel to the surface of said tissue site and are angled relative to said plane;

a generally planar substrate encapsulated within said base, said substrate having a first side and a second side, said detector and said emitter mounted to said substrate proximate said probe first portion and said emitter and said detector are mounted on the same side of said substrate; and a light shield separating said emitter and said detector, whereby light transmitted from said emitting region is received at said light collecting region after passing through said tissue site.

8. The sensor of claim 7 wherein said base further comprises a light absorbing material proximate a base surface that contacts said tissue site.

9. A sensor comprising:

a base;

a probe having a first portion proximate said base and a second portion distal said base embeddable within a tissue site;

a light emitting region of said probe second portion; and a light collecting region disposed in said second probe portion and spaced from said light emitting region, so that said light emitting region and said light collecting region are in a plane substantially parallel to the surface of said tissue site and are angled relative to said plane;

a generally planar substrate encapsulated within said base, said substrate having a first side and a second side, said detector and said emitter mounted to said substrate proximate said probe first portion, wherein said detector and said emitter are mounted to said substrate second side, said probe first portion extending through said substrate from said first side to said second side so that light transmitted from said emitter is reflected within said probe to said light emitting region and light received at said light collecting region is reflected within said probe to said detector; and a light shield separating said emitter and said detector, whereby light transmitted from said emitting region is received at said light collecting region after passing through said tissue site.

10. The sensor of claim 9 wherein said emitter and said detector are mounted generally flush to said substrate second side.

11. The sensor of claim 10 wherein said emitter and said detector are end-mounted to said substrate second side.

12. A pulse oximetry sensor method comprising the steps of:

embedding an emitting region of an embeddable member within a tissue site positioning a detector proximate to said tissue site so as to receive light passing through said tissue site from said emitting region, where a light collecting region of said detector is of substantially greater area than said emitting region; and transmitting light from an emitter located proximate said tissue site and said detector through said embeddable member to said emitting region so that light from said emitting region illuminates said site.

13. The pulse oximetry sensor method of claim 12 further comprising the step of shielding said detector from said emitter so that said detector substantially receives light only after passing through said tissue site.

14. A pulse oximetry sensor method comprising the steps of:

embedding an emitting region within a tissue site so that light from said emitting region illuminates said site;

embedding a collecting region within said tissue site distal said emitting region so as to receive light passing through said tissue site from said emitting region, said emitting region and said collecting region angled away from a surface of said tissue site;

transmitting light from an emitter located proximate said tissue site to said emitting region;

transmitting light to a detector located proximate said tissue site from said collecting region; and absorbing light from said emitting region that is reflected from said surface so that substantially no such reflected light is received at said collecting region.

15. The pulse oximetry sensor method of claim 14 further comprising the step of shielding said detector from said emitter so that said detector substantially receives light only after passing through said tissue site.

16. The pulse oximetry sensor method of claim 14 further comprising the step of heating said tissue site so as to stimulate the flow of arterial blood to said tissue site.

17. The pulse oximetry sensor method of claim 14 further comprising the step of applying a vasodilating substance to said tissue site so as to stimulate the flow of arterial blood to said tissue site.

18. A pulse oximetry sensor method comprising the steps of:

measuring a first intensity ratio from a first pair of wavelengths illuminating a tissue site;

measuring a second intensity ratio from a second pair of wavelengths illuminating said tissue site;

applying a first calibration curve to said first intensity ratio to yield a first saturation value;

applying a second calibration curve to said second intensity ratio to yield a second saturation value; and detecting a low blood fraction condition at said tissue site from the difference between said first saturation value and said second saturation value.

19. A pulse oximetry sensor comprising:

an emitting means for illuminating a tissue site;

a collecting means for receiving light from said emitting means after passing through said tissue site so as to measure characteristics of said tissue site, said collecting means comprising a detecting means attachable proximate said tissue site;

a probe means for embedding at least a portion of said emitting means within said tissue site and for attaching said collecting means distal said emitting means, said emitting means comprising a light generating means attachable proximate said tissue site and a transmitting means for conveying light from said generating means to a light emitting region of said probe means; and a shielding means for blocking direct light between said light generating means and said detecting means.

20. The pulse oximetry sensor of claim 19 further comprising an angling means for measuring tissue layers distal said probe means.

21. The pulse oximetry sensor of claim 20 further comprising:
- a transmitting means for conveying light from a light generating means attachable proximate said tissue site to a light emitting region of said probe means; and
- a receiving means for conveying light from a light collecting region of said probe means to a light detecting means attachable proximate said tissue site.

22. The pulse oximetry sensor of claim 21 further comprising an absorbing means for preventing light from reaching said light collecting region after reflection from the surface of said tissue site.

23. The pulse oximetry sensor of claim 21 further comprising a shielding means for blocking direct light between said light generating means and said light detecting means.

* * * * *

UNITED STATES PATENT AND TRADEMARK OFFICE
CERTIFICATE OF CORRECTION

PATENT NO. : 6,285,896 B1
DATED : September 4, 2001
INVENTOR(S) : Tobler et al.

It is certified that error appears in the above-identified patent and that said Letters Patent is hereby corrected as shown below:

Column 16,
Line 65, please delete the claim in its entirety and replace it with the following:
-- A pulse oximetry sensor comprising:
    an emitting means for illuminating a tissue site;
    a collecting means for receiving light from said emitting means after passing through said tissue site so as to measure characteristics of said tissue site; and
    a probe means for embedding at least a portion of said emitting means within said tissue site and for attaching said collecting means distal said emitting means; and
    an angling means for measuring tissue layers distal said probe means. --

Signed and Sealed this

Eleventh Day of June, 2002

Attest:

Attesting Officer

JAMES E. ROGAN
Director of the United States Patent and Trademark Office